(12) United States Patent
Graham

(10) Patent No.: US 6,984,126 B1
(45) Date of Patent: Jan. 10, 2006

(54) ORTHODONTIC CRIMPING PLIERS

(76) Inventor: Neil John Graham, 6017 Lido La., Long Beach, CA (US) 90803

( * ) Notice: Subject to any disclaimer, the term of this patent is extended or adjusted under 35 U.S.C. 154(b) by 0 days.

(21) Appl. No.: 10/893,098

(22) Filed: Jul. 16, 2004

(51) Int. Cl.
 *A61C 3/00* (2006.01)
 *A61C 3/16* (2006.01)

(52) U.S. Cl. ............................. 433/4; 433/159; 81/418

(58) Field of Classification Search ................. 433/4, 433/6, 159; 81/418; 606/207; D8/52
 See application file for complete search history.

(56) References Cited

U.S. PATENT DOCUMENTS

| | | | |
|---|---|---|---|
| 340,896 A | | 4/1886 | Starr |
| 634,493 A | | 10/1899 | Bradley |
| 867,296 A | * | 10/1907 | Park ........................ 119/806 |
| 1,103,696 A | * | 7/1914 | Montag ..................... 431/251 |
| 1,304,720 A | | 5/1919 | Young |
| 1,316,409 A | | 9/1919 | Bahre |
| 1,338,043 A | * | 4/1920 | Sandin ........................ 29/248 |
| 1,670,361 A | * | 5/1928 | Johnson ...................... 433/23 |
| 2,806,394 A | * | 9/1957 | Briegel ..................... 72/409.19 |
| 2,959,858 A | * | 11/1960 | Drake .......................... 433/4 |
| 3,727,316 A | | 4/1973 | Goldberg |
| 3,911,583 A | | 10/1975 | Hoffman |
| 4,189,839 A | * | 2/1980 | Manuel ........................ 433/4 |
| 4,274,415 A | * | 6/1981 | Kanamoto et al. .......... 606/142 |
| 4,799,884 A | * | 1/1989 | Bergersen ..................... 433/6 |
| 4,892,478 A | * | 1/1990 | Tateosian et al. ............. 433/6 |
| 5,084,935 A | | 2/1992 | Kalthoff |
| 5,197,880 A | | 3/1993 | Lovaas |
| D368,212 S | * | 3/1996 | Johnston ..................... D8/52 |
| 5,538,421 A | | 7/1996 | Aspel |
| 5,588,832 A | | 12/1996 | Farzin-Nia |
| 5,732,461 A | * | 3/1998 | Keffeler et al. .............. 29/751 |
| 6,293,790 B1 | | 9/2001 | Hilliard |
| 6,745,651 B2 | * | 6/2004 | Porter ....................... 81/426.5 |

* cited by examiner

*Primary Examiner*—Ralph A. Lewis
(74) *Attorney, Agent, or Firm*—Neil John Graham

(57) ABSTRACT

Pliers adapted to lock wires within thermoformed dental appliances following the partial enclosure of wires during the thermoforming process.

4 Claims, 6 Drawing Sheets

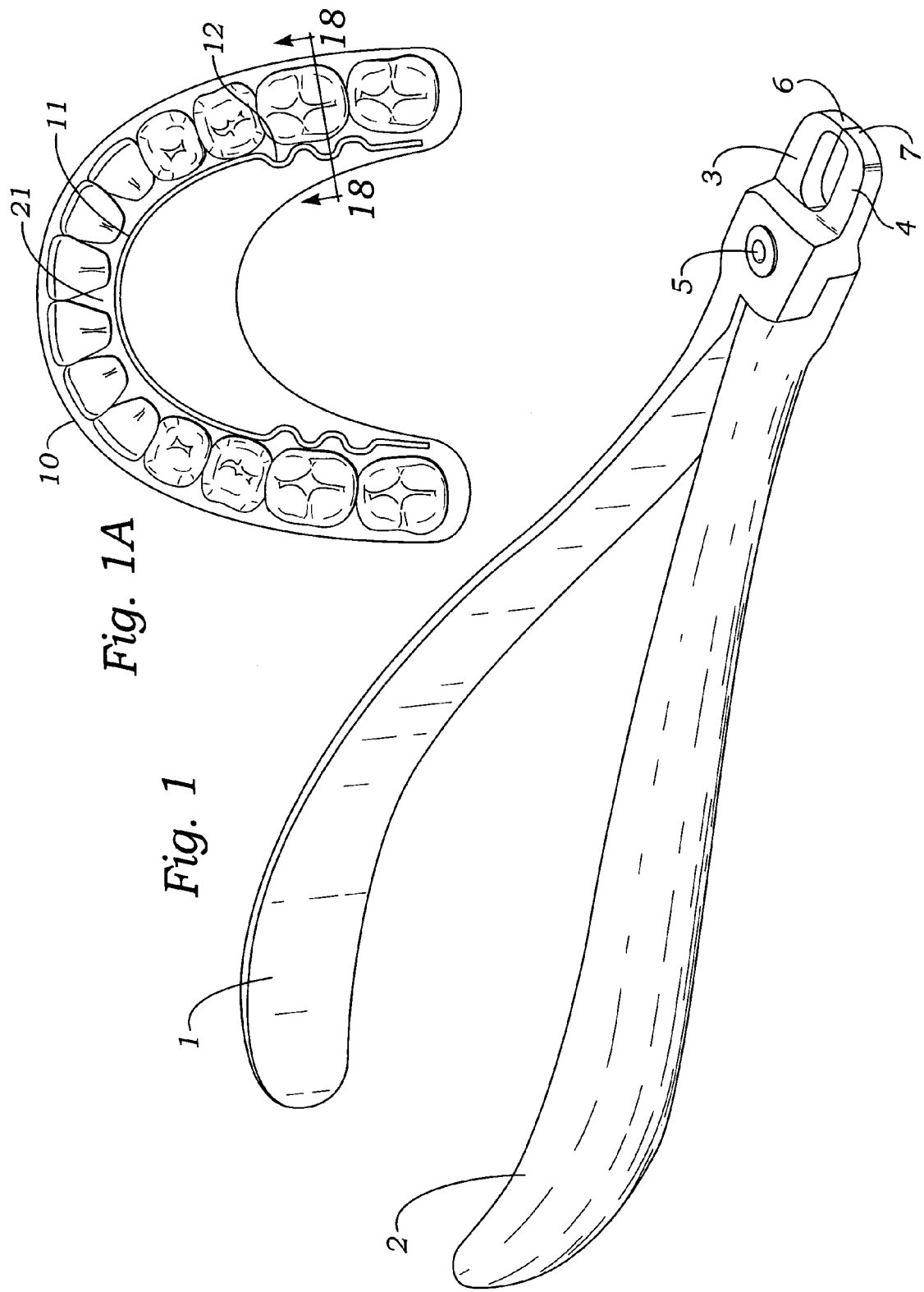

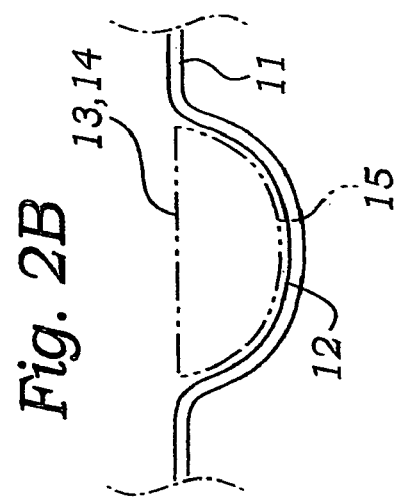
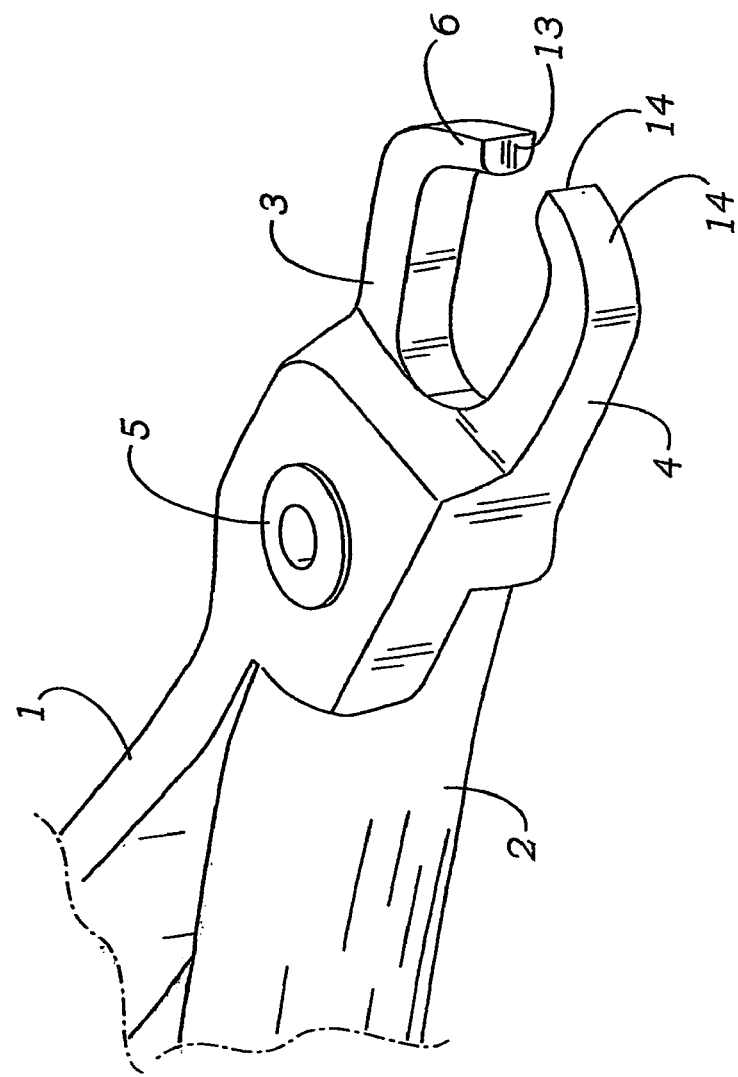

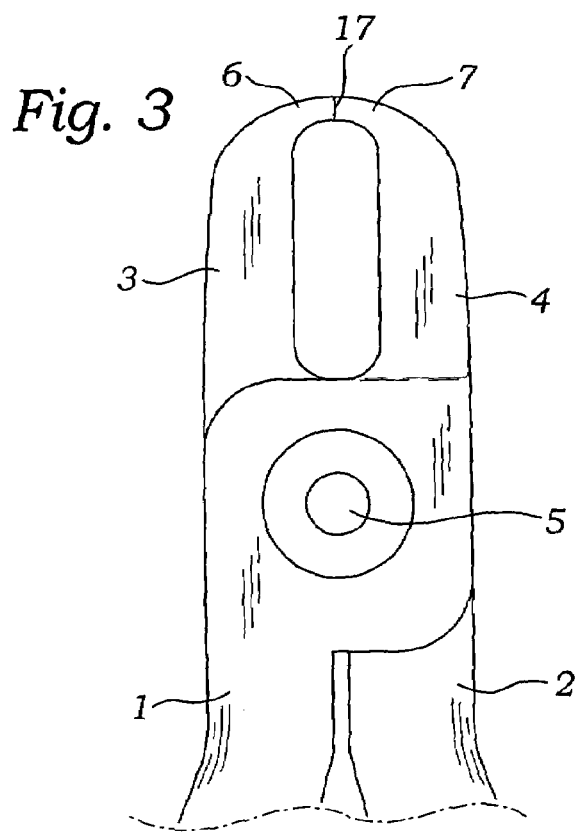
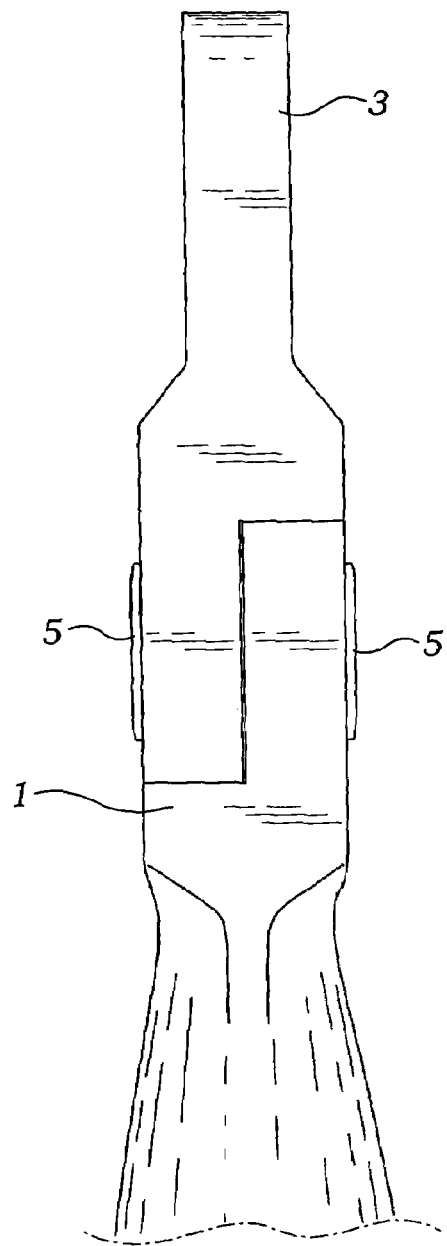
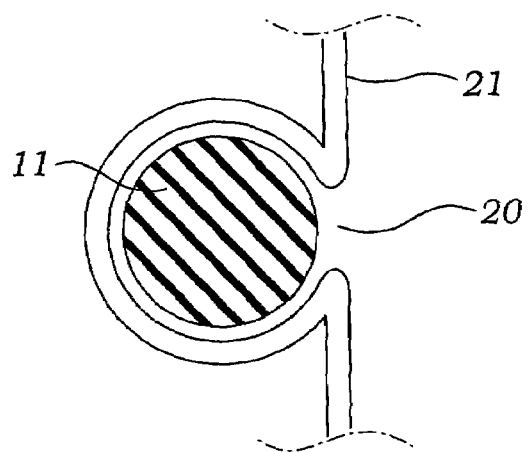

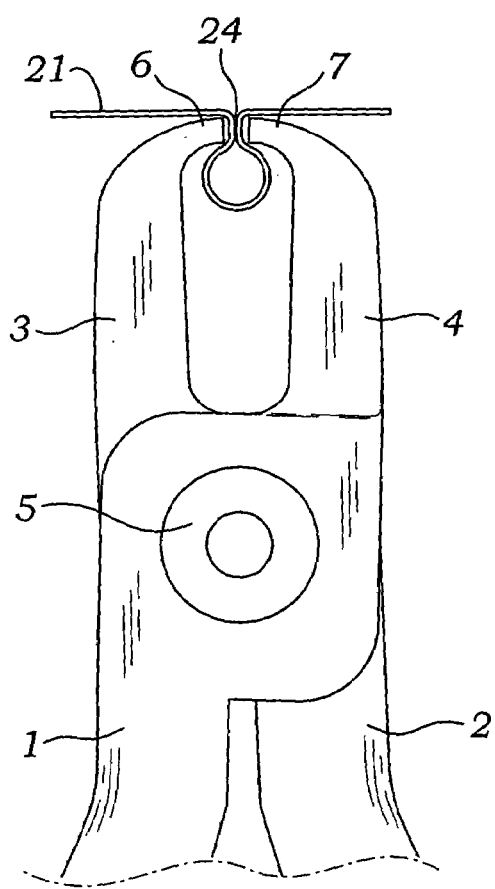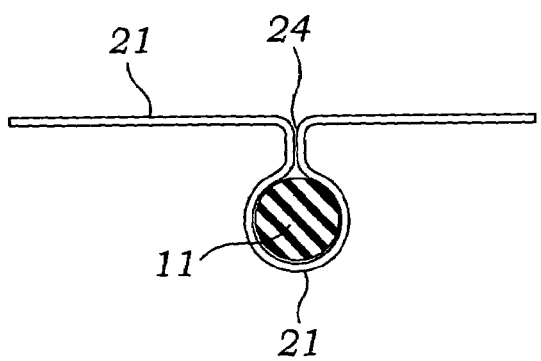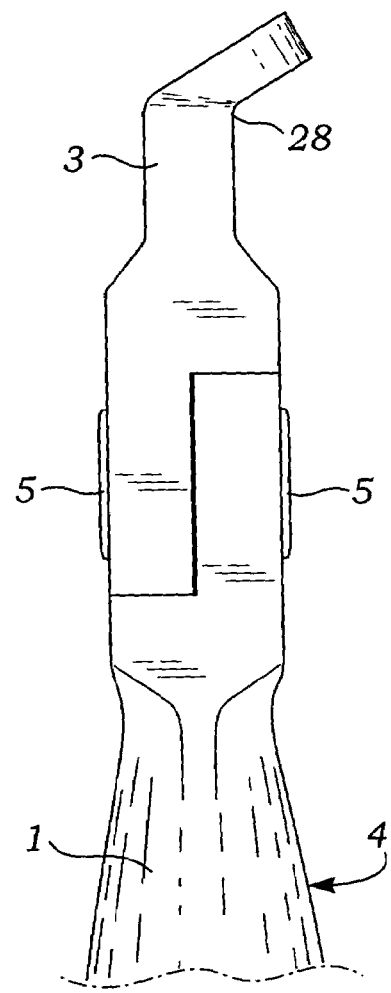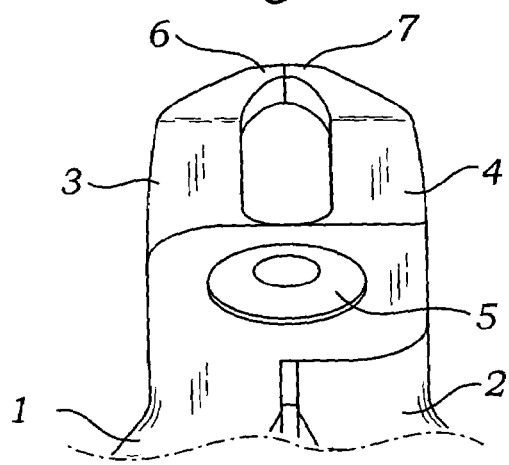

ORTHODONTIC CRIMPING PLIERS

FIELD OF THE INVENTION

The present invention relates generally to dental instruments. More specifically, the invention is directed to pliers which aid in locking specially configured wires within thermoformed dental appliances.

DESCRIPTION OF RELATED ART

In the field of orthodontics thermoformed appliances are used extensively. There is a desirability of enclosing wires within the thermoplastic materials. Enclosed wires can have such functions as stabilizing the thermoformed material or providing an attachment for devices attached to the teeth, such as Adams clasps. The problem is the vacuum pressure thermoformed process does not readily enclose the wires. A two-step process for enclosing the wires may be used for thermoformed materials. Liquid acrylic may be placed around the wire just prior to vacuum pressure forming the thermoplastic material over the wire. This process is not possible for polypropylene due to the fact that it does not adhere to acrylic. U.S. Pat. No. 4,798,534 by Breads describes a process of holding the wire away from a model surface which enhances the wire being enclosed in the thermoplastic material. In pending U.S. Pub. No. 20030219690 an arcuate wire is described enclosed in polypropylene thermoformed appliances wherein repeated curves in the wire extending away from the dental model surface are used to achieve the locking of the wire. The enclosure of the curved sections of the arcuate wire is not consistent which leads to the present invention.

What is needed are orthodontic pliers that complete the enclosure of the thermoformed material around the curved portions of the arcuate wire, or, in a more general sense, around a partially enclosed wire. Further, this protrusion produced by the pliers must not protrude upon the patient's gums or teeth.

U.S. Pat. No. 340,896 describes an orthodontic band contouring plier with curved male and female jaws. The pliers are distinguishable for being limited to producing a curvature to an orthodontic band.

U.S. Pat. No. 634,493 discloses a patent with two parallel jaws.

U.S. Pat. No. 1,304,720 discloses a plier for holding band material. The pliers are distinguishable by having a first straight jaw with a hole in it and a curved male jaw which enters the hole of the first jaw when the plier is closed. No joint is formed.

U.S. Pat. No. 1,316,409 discloses a plier for extracting a cotter pin. The pliers are distinguishable by having male and female jaws.

U.S. Pat. No. 3,727,316 discloses parallel jaws with notches for guides to bend wires. There are no male jaws.

U.S. Pat. No. 3,911,583 issued on Oct. 14, 1975, to Robert Hoffman describes dental pliers having an upper jaw having upwardly and inwardly tapered concave shaped sides and front for forming gripping edges in removing metal bands cemented to teeth and the removal of cement on teeth. The pliers are distinguishable for being limited to removal of cemented dental bands and cement.

U.S. Pat. No. 5,084,935 issued on Feb. 4, 1992, to Ferdinand Kalthoff describes a multiple-purpose wire shaping and cutting tool. It further describes means of forming certain commonly known wire shapes used in the orthodontic profession. There are opposing convex and concave surfaces on its inner jaws in order for the tool to perform its intended function. One handle has a hole while the other handle has a disc-shaped guide for forming labial bows in a wire.

U.S. Pat. No. 5,197,880 issued on Mar. 30, 1993, to Leeland M. Lovaas describes a tool for crimping a metal endodontic file. The tool has opposing convex and concave surfaces on its inner jaws to perform its intended function. Unlike the present invention, the inner surfaces of the jaws are parallel to one another when the tool is in its closed position. The file crimping tool of FIG. 8 is distinguishable because the tool cannot be used for the enclosing of wires in thermoplastic retainers.

U.S. Pat. No. 5,538,421 issued on Jul. 23, 1996, to Thomas E. Aspel describes an assortment of dental pliers comprising a lower jaw longer or shorter than the upper jaw for removing orthodontic brackets, bands, buttons, cleats, bonding materials, and braces from teeth. The pliers are distinguishable for being limited to jaws designed for cutting and removing unwanted dental materials from the patient's teeth and to prevent luxation (tipping) of the tooth to minimize pain while using the pliers.

U.S. Pat. No. 5,588,832 issued on Dec. 31, 1996, to Farrokh Farzin-Nia describes a method of fabricating orthodontic pliers and the stainless steel or titanium alloy pliers made by the process. The manufacturing process of making these pliers minimizes the grinding and cutting of the pliers once the two nearly identical halves are made into the two scissor parts. The orthodontic pliers are distinguishable for having conventional needle-nose jaws.

U.S. Pat. No. 6,293,790 describes pliers for crimping an encapsulated expansion screw wherein the jaw arms are equal in length and similar in having an arcuate shape. This is unlike the present invention in that it does not produce a butt joint. The arcuate shape produces a point of the material which will not complete the enclosure of an embedded wire.

None of the above inventions and patents, taken either singly or in combination, is seen to describe the instant invention as claimed.

SUMMARY OF THE INVENTION

The present invention is crimping pliers used in orthodontics. It is the object of this invention to provide a plier-type hand tool for orthodontists and orthodontic technicians which has the means of improving the enclosure of a wire within a thermoformed orthodontic appliance. The goal is to press the two layers of thermoplastic material together into a butt joint, completing the enclosure of the wire. The crimping pliers are comprised of two elongated components that are subapically and pivotally joined with a pivot pin. Each of these elongated pieces is irregular in shape, equal in length and possesses symmetrical opposing jaws relative to each other. Each jaw portion of the crimping pliers ends with a right angled extension extending towards the opposite jaw. The right angled extensions end with jaw tips which are mutually parallel and fit together when the plier jaws are closed. A butt joint is formed when two layers of thermoplastic material are placed between the parallel jaw tips and the plier jaws are closed. In the preferred embodiment the pliers are designed to complete the enclosure of a partially embedded, specially formed, 0.045" wire. The 045" wire is arcuate in form and is placed in the palatal and lingual portion of the thermoformed orthodontic appliance. The 0.045 wire has repeated arc type bends which extend away from surface of the patient's mouth or the inner surface of the retainer. The purpose of these bends is to facilitate the enclosure of the wire by the thermoplastic material during the vacuum pressure-forming process. Each parallel jaw tip is the shape of a half circle. The arc portion of the half circle faces the handles of the pliers and is shaped to conform to the inner arc of the wire. The pliers are designed to reach over the partially enclosed wire in the arc areas and press the thermoformed material together in the inner part of the arc. The flat surface faces the tissue surface of the appliance or the apex of the pliers. The importance of the flat surface is to produce a protrusion of the thermoplastic material that will not protrude upon the patient's soft tissue or teeth when the orthodontic appliance is worn. In another embodiment of the above pliers the jaws of the pliers turn 60° from the long axis of the pliers in the axial direction of the pivot pin.

It is another object of this invention to provide an orthodontic crimping plier to enclose a wire which has been vacuum-formed over, but lies on the surface of the dental model. In this embodiment the pliers are similar to the above pliers except the parallel jaw tips are rectangular in shape, the longitudinal dimension of the rectangular tip is in the longitudinal direction of the 0.045" wire. The object is to enclose the wire and not protrude upon the patient's soft tissue and teeth. In this embodiment the jaws may be either straight or turn 60°.

BRIEF DESCRIPTION OF THE DRAWINGS

FIG. 1 is a perspective view of the orthodontic crimping pliers;

FIG. 1A is a perspective view of the orthodontic crimping pliers with a thermoformed dental retainer;

FIG. 2A is a prospective view of the pliers of FIG. 1 in an open position;

FIG. 2B is a perspective view of the end of the jaw extension of the pliers of FIG. 1 in relation with a curved portion of an imbedded wire;

FIG. 3 is side plan view of the pliers of FIG. 1 in an open position;

FIG. 4 is a top plan view of the pliers of FIG. 1;

FIG. 5 is a cross-sectional view of the pliers of FIGS. 1 through 18 and 18;

FIG. 6 is a perspective view of FIG. 5 with the side plan view of the pliers in FIG. 1 enclosing the wire with the thermoplastic material;

FIG. 7 is a cross-sectional view of the thermoplastic material pressed over the wire in FIG. 6;

FIG. 8 is a top plan view of the pliers in FIG. 1 in another embodiment with a 60° bend in the jaws of the pliers;

FIG. 9 is a prospective view of the pliers of FIG. 8;

DETAILED DESCRIPTION OF THE PREFERRED EMBODIMENTS

Figure 10:
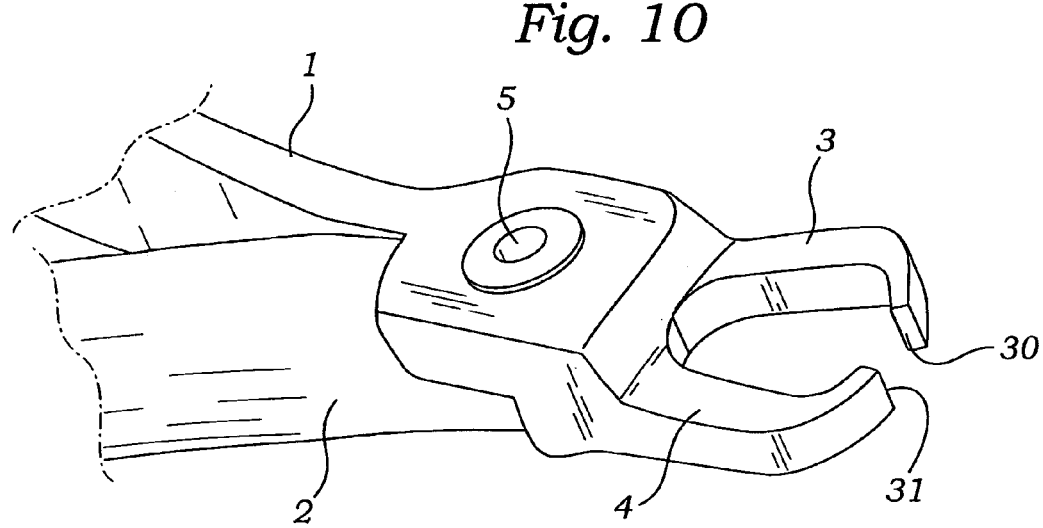
FIG. 10 is a prospective view of another embodiment of the orthodontic crimping pliers in an open position.
Figure 10A:
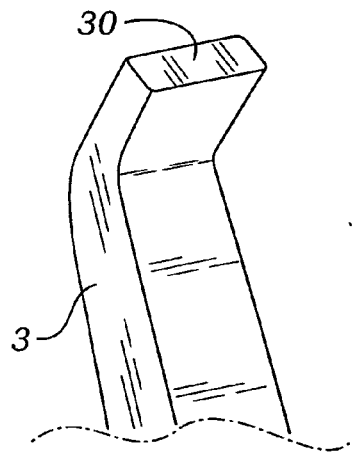
FIG. 10A is a prospective view of the end of the orthodontic crimping pliers shown in FIG. 10.

The present invention is a pair of orthodontic crimping pliers for enclosing wires within thermoplastic retainers. Referring to FIGS. 1, 2A, 2B, 3, 4, 6, 8, 9, 10, 10A, 11, 12, and 13 the orthodontic crimping pliers are comprised of a first handle 1 continuous with a first jaw 4, a second handle 2 continuous with a second jaw 3 and a pivot pin 5 joining the two jaw/handle combinations together pivotally. FIGS. 1 and 1A depict the orthodontic crimping pliers with a thermoplastic retainer 10 with an embedded wire 11. The embedded wire 11 is depicted with repeating curves 12 which curve away from the inner surface of the retainer 10. The curved wire 11 areas 12 are designed to facilitate the enclosure of the wire 11 by the thermoplastic material 21 during the vacuum-pressure thermoforming process. The pliers in FIGS. 1, 2A, 2B, 3, 4, 6, 8 and 11 are designed to fit the wire arc 12 and press the thermoplastic material 21 in the curved area 12. In FIG. 5 the wire 12 is shown prior to full enclosure 20 and in FIGS. 6, 7 and 11 the wire 12 is shown enclosed 24 in FIGS. 6 and 7. FIG. 1 depicts the jaws 3 and 4 having right angle extensions 6 and 7 each extending towards the opposing jaw and ending in a tip. The tip of each right angle jaw 6 and 7 has a flat surface 13 and 14 with a half circle shape as shown in FIGS. 2A and 2B, the curved portion 15 of the half circle facing the handles 1 and 2 of the pliers. The curved portion 15 of the half circle, as shown in FIG. 2B, is designed to conform to the curvature of the curved portion 12 of the 0.045" wire 11 as shown in FIG. 2B. The inner flat surfaces of the half circles 13 and 14 conform to the inner surface or tissue side of the retainer 10. When the handles 1 and 2 are squeezed, as in FIG. 3, the flat surfaces 13 and 14 are closed over the thermoplastic material 21 to enclose the 0.045" wire 11 wherein the gap 20 in FIG. 5 is closed or pressed 24 as in FIGS. 6, 7 and 11. FIG. 4 shows a top view of the pliers wherein the pliers have the jaws 3 and 4 in the same axial direction as the handles 1 and 2.

FIG. 7 is an enlargement of FIG. 6 depicting the retainer material 21 enclosing the wire 11 The pliers have pressed 24 the retainer 10 material 21 enclosing the wire 11. FIG. 8 shows another embodiment of the orthodontic crimping pliers of FIGS. 1, 2A and 2B, the jaws 3 and 6 bending 28 60° from the longitudinal direction of the handles 1 and 2 in the axial direction of the pivotal pin 5. FIG. 9 depicts the pliers in FIG. 8 from a different perspective. The 60° angled jaws 3 and 4 in FIGS. 8 and 9 allow easier access to certain areas of the retainer 10.

Figure 11:
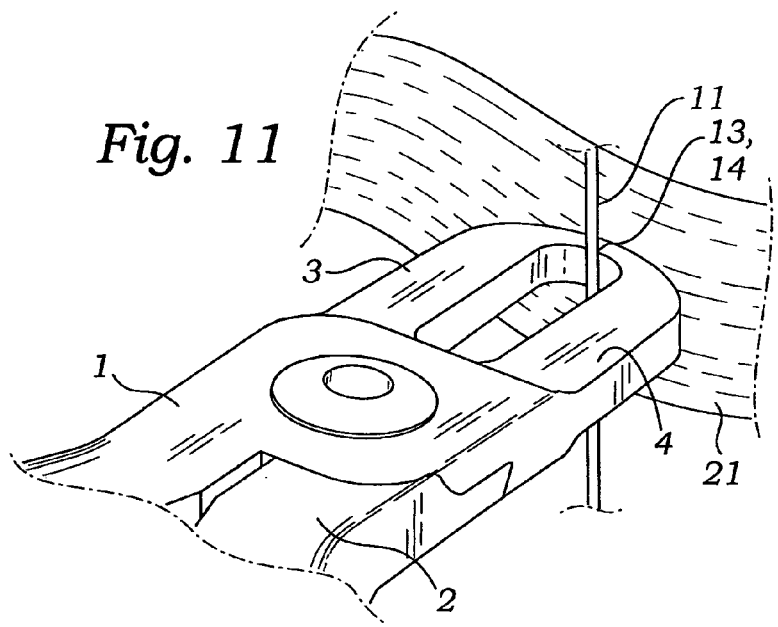
FIG. 11 is a perspective view of the pliers of FIG. 10 in a closed position pressing the thermoplastic material over the embedded wire.
Figure 12:
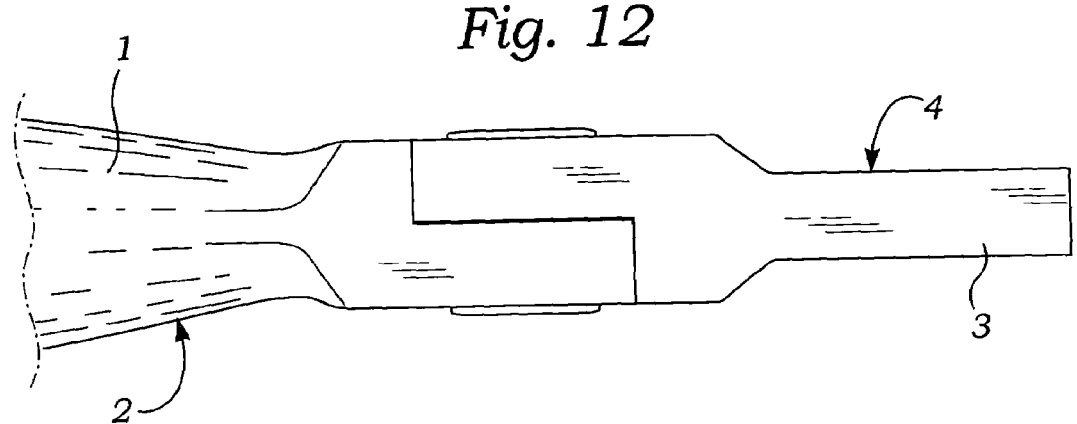
FIG. 12 is a top plan view of the pliers in FIG. 10.

Referring to FIGS. 10, 11 and 12, another embodiment of the pliers is shown wherein the flat surfaced 30 and 31 tips of the right angled jaw extensions which press the retainer material 21 are rectangular in shape wherein the length of the rectangle is in the longitudinal direction of the wire 11 when the pliers are used to lock the retainer material 21 over the wire 11 as shown in FIG. 11. The rectangular designs of the flat surfaces 30 and 31 are useful for locking a straight wire which is at the level of the inner surface of the retainer without protruding the retainer material 21 into the tissue of the patient while wearing the retainer 10. FIG. 12 depicts the top view of this embodiment with the jaws 3 and 4 in the same longitudinal direction as the handles 1 and 2.

Figure 13:
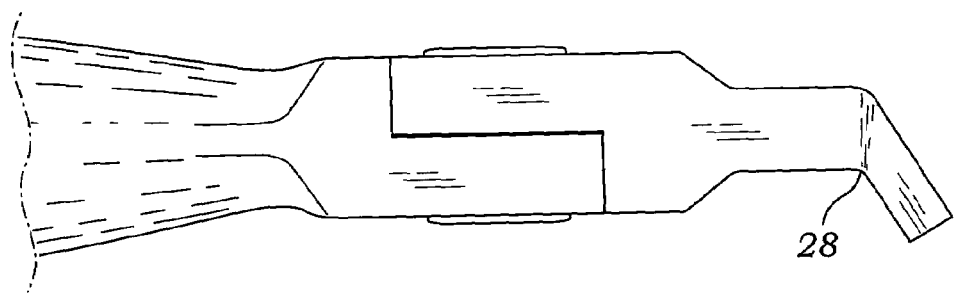
FIG. 13 is a top plan view of the pliers of FIG. 10 in another embodiment with the jaws bent 60°.

FIG. 13 depicts another embodiment wherein the pliers of FIGS. 10, 11 and 12 have jaws 3 and 4 with a 60° bend from the longitudinal axis of the handles 1 and 2 of the pliers and in the axial direction of the pivotal pin 5. This embodiment enables access to certain areas of the retainer.

The invention has been described with specific embodiments. However, the intent of the invention is to provide orthodontic crimping pliers that complete the enclosure of a partially enclosed wire within a thermoformed orthodontic appliance. The orthodontic crimping pliers produce a butt joint of the thermoplastic material which prevents the enclosed wire from being dislodged from the thermoplastic material.

What is claimed is:

1. Orthodontic crimping pliers for completing the enclosure of a wire within the thermoplastic material of an orthodontic appliance comprising:
   a longitudinal first member having a first handle at one end and a first jaw with an apex at the opposite end;
   a longitudinal second member having a second handle at one end and a second jaw with an apex at the opposite end;
   a pivot pin connecting the first and second members pivotally wherein the first and second members cross so that the jaw portions are opposite each other and can be moved toward and away from each other into respective closed and open positions substantially along an imaginary plane by manipulating the handles about a longitudinal axis;
   right angle projections at the ends of the first and second jaws, each directed to the right angled projection of the opposite jaw and ending in a tip; and
   half circle flat tips on each right angle projection with the circle portion of the half circle facing the pivotal pin, wherein the flat tips fit together when the first and second jaws are brought together, the half circle adapted to fit the curved portion of an embedded wire with the thermoplastic material.

2. An orthodontic crimping pliers according to claim 1 wherein the first and second jaws are curved 60 degrees from the long axis of the pliers.

3. An orthodontic crimping pliers according to claim 1 wherein the diameters of the half circle ends are 3 mm.

4. A method of enclosing a partially enclosed wire in a thermoplastic orthodontic retainer using orthodontic crimping pliers comprising:
   opening the jaws of the orthodontic crimping pliers;
   placing the open plier jaws over the thermoplastic material side of the partially enclosed wire pushing the projections of the jaws of the pliers past the wire; and
   squeezing the handles of the pliers until the jaw projections meet forming a butt joint of the thermoplastic material which completes the enclosure of the wire.

* * * * *